United States Patent
Kucklick et al.

(10) Patent No.: US 7,445,596 B2
(45) Date of Patent: Nov. 4, 2008

(54) ATRAUMATIC ARTHROSCOPIC INSTRUMENT SHEATH

(75) Inventors: Theodore R. Kucklick, San Jose, CA (US); Martin Trieb, Cloverdale, CA (US)

(73) Assignee: Cannuflow, Inc., San Jose, CA (US)

( * ) Notice: Subject to any disclaimer, the term of this patent is extended or adjusted under 35 U.S.C. 154(b) by 462 days.

(21) Appl. No.: 11/031,149

(22) Filed: Jan. 7, 2005

(65) Prior Publication Data

US 2005/0203342 A1 Sep. 15, 2005

Related U.S. Application Data

(63) Continuation-in-part of application No. 10/769,629, filed on Jan. 29, 2004.

(51) Int. Cl.
*A61B 1/015* (2006.01)
(52) U.S. Cl. .................. 600/114; 600/156; 600/128; 604/164.02
(58) Field of Classification Search ................ 600/114, 600/128, 153, 156, 130; 604/164.02
See application file for complete search history.

(56) References Cited

U.S. PATENT DOCUMENTS

| 4,491,132 | A | | 1/1985 | Aikins |
| 4,646,722 | A | | 3/1987 | Silverstein et al. |
| 4,674,500 | A | | 6/1987 | DeSatnick |
| 4,721,097 | A | | 1/1988 | D'Amelio |
| 4,886,049 | A | | 12/1989 | Darras et al. |
| 4,897,079 | A | | 1/1990 | Zaleski et al. |
| 4,973,321 | A | * | 11/1990 | Michelson ............... 604/523 |
| 5,184,602 | A | | 2/1993 | Anapliotis et al. |
| 5,273,545 | A | | 12/1993 | Hunt et al. |
| 5,337,734 | A | | 8/1994 | Saab |
| 5,386,817 | A | | 2/1995 | Jones |
| 5,413,092 | A | | 5/1995 | Williams, III et al. |
| 5,415,157 | A | | 5/1995 | Welcome |
| 5,458,606 | A | * | 10/1995 | Cohen et al. ............. 606/108 |
| 5,483,951 | A | | 1/1996 | Frassica et al. |
| 5,527,276 | A | | 6/1996 | Bruce |
| 5,571,128 | A | | 11/1996 | Shapiro |
| 5,575,753 | A | | 11/1996 | Yabe et al. |
| 5,575,756 | A | | 11/1996 | Karasawa et al. |
| 5,593,394 | A | * | 1/1997 | Kanesaka et al. .......... 604/524 |
| 5,601,603 | A | * | 2/1997 | Illi ........................ 606/213 |
| 5,637,075 | A | * | 6/1997 | Kikawada ................ 600/153 |
| 5,762,604 | A | | 6/1998 | Kieturakis |
| 5,797,882 | A | * | 8/1998 | Purdy et al. ............. 604/164.09 |
| 5,800,409 | A | | 9/1998 | Bruce |

(Continued)

OTHER PUBLICATIONS

Linvatek Product Brochure, Spring/Summer Edition 2000.

*Primary Examiner*—John P Leubecker
(74) *Attorney, Agent, or Firm*—Susan L. Crockett, Esq.; Crockett & Crockett

(57) ABSTRACT

An arthroscopic inflow and outflow sheath providing an improved inflow and outflow system reducing the diameter of a continuous flow system while eliminating the need for a third portal during arthroscopy. The improved arthroscopic inflow and outflow sheath comprises an elongated atraumatic sheath having an inner surface, outer surface, proximal end, and distal end. The atraumatic sheath further comprises plurality of ribs or webs extending from the inner surface of the sheath and designed to contact an outer surface of the arthroscope creating outer lumens facilitating the inflow and outflow of fluid to a surgical site.

18 Claims, 6 Drawing Sheets

U.S. PATENT DOCUMENTS

| | | |
|---|---|---|
| 5,947,990 A | 9/1999 | Smith |
| 5,989,183 A | 11/1999 | Reisdorf et al. |
| 6,110,103 A | 8/2000 | Donofrio |
| 6,126,592 A | 10/2000 | Proch et al. |
| 6,174,280 B1 | 1/2001 | Oneda |
| 6,293,909 B1 | 9/2001 | Chu et al. |
| 6,315,714 B1 | 11/2001 | Akiba |
| 6,447,446 B1 | 9/2002 | Smith et al. |
| 6,558,379 B1 | 5/2003 | Batchelor et al. |
| 7,150,713 B2 * | 12/2006 | Shener et al. ............... 600/156 |
| 2002/0173699 A1 | 11/2002 | Becker et al. |
| 2003/0018340 A1 | 1/2003 | Branch |
| 2005/0043690 A1 | 2/2005 | Todd |

* cited by examiner

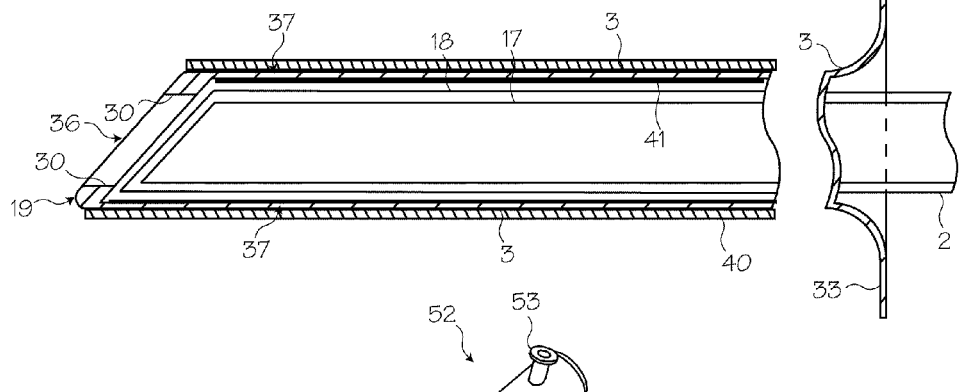
Fig. 5
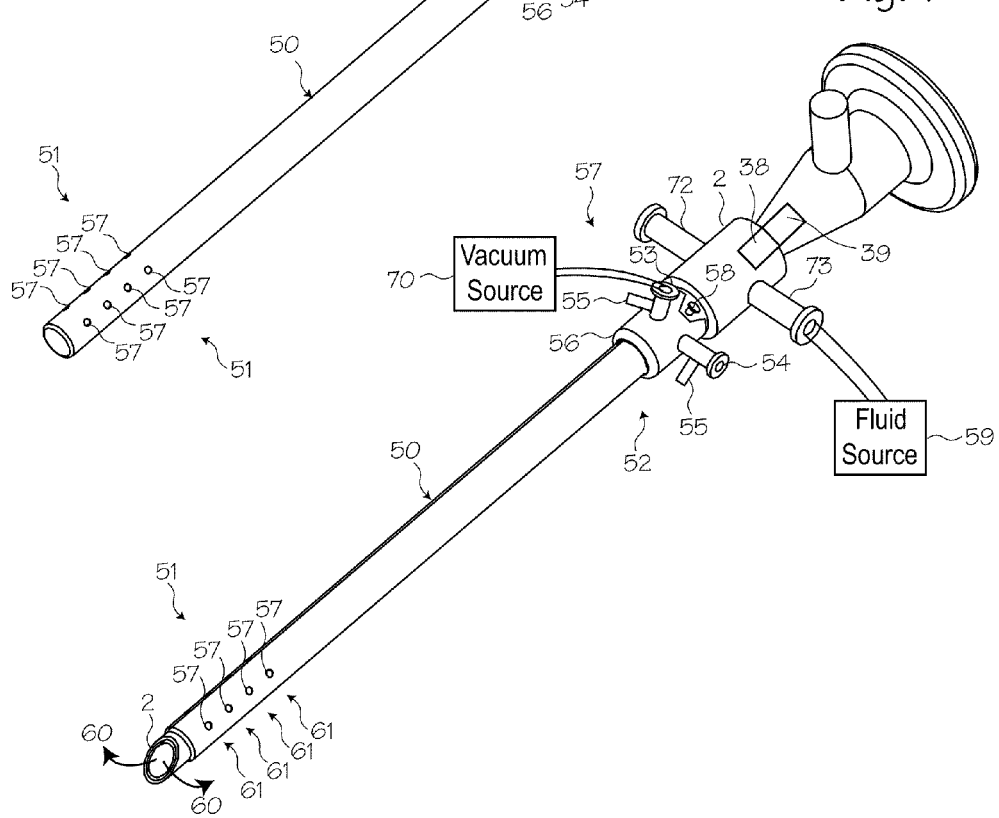
Fig. 6
Fig. 7

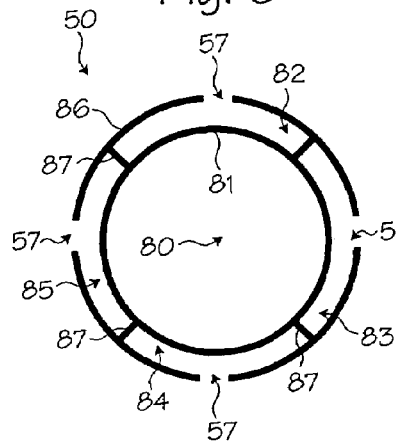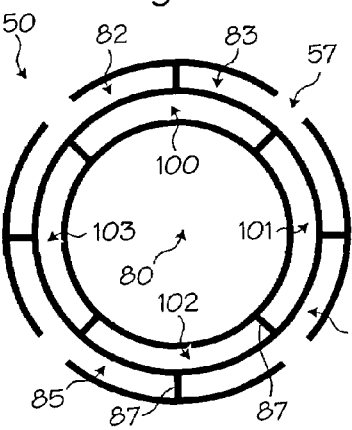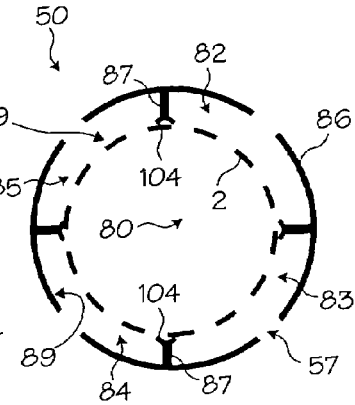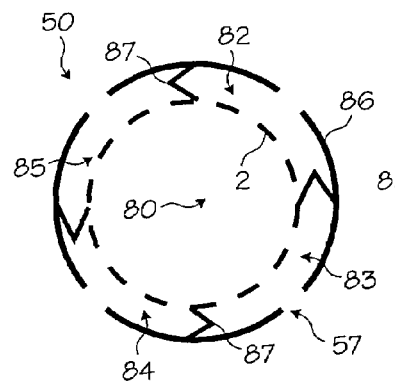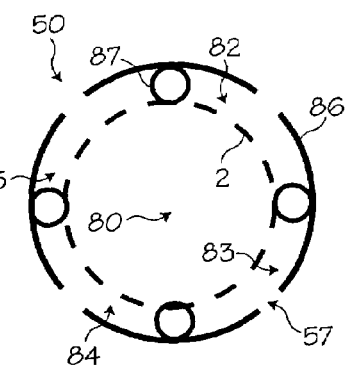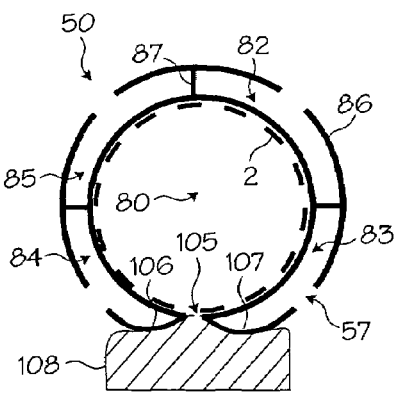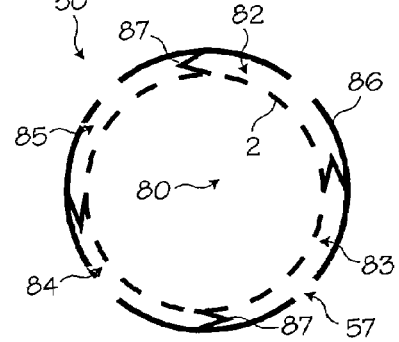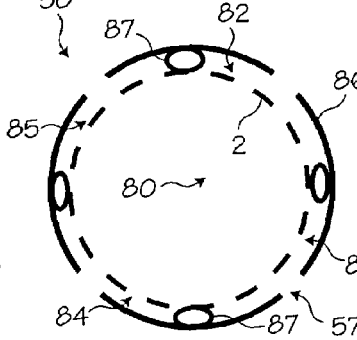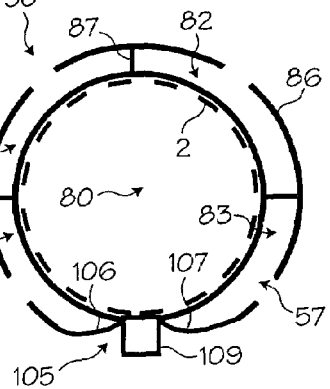

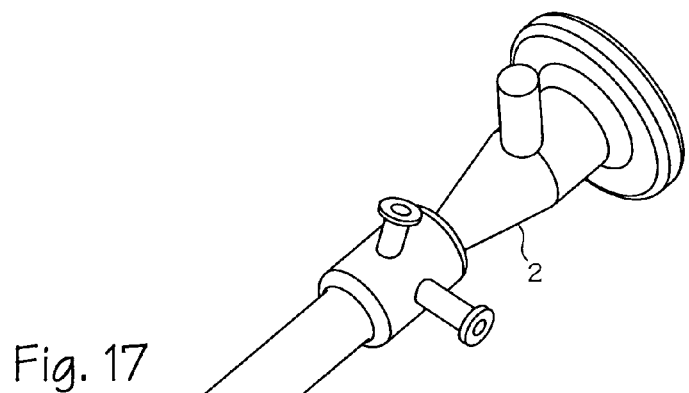
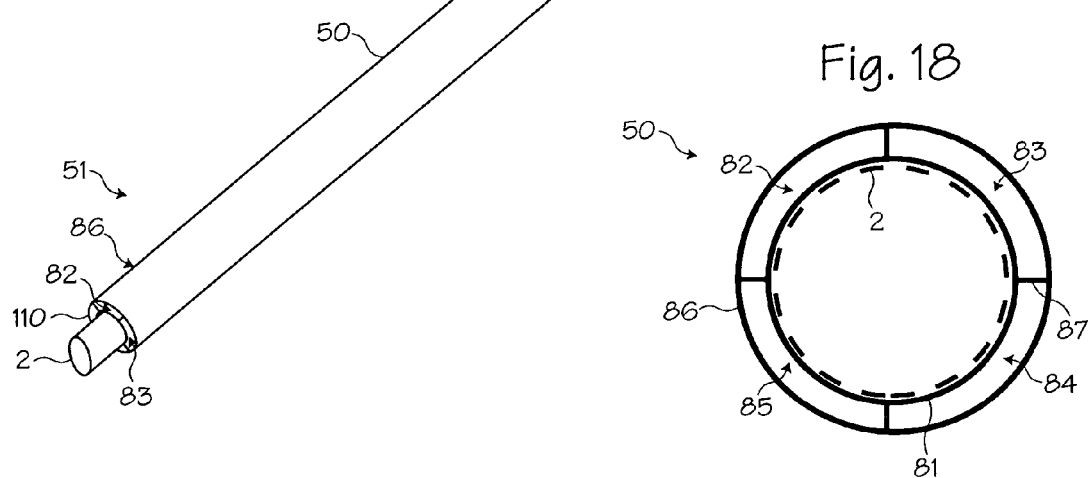
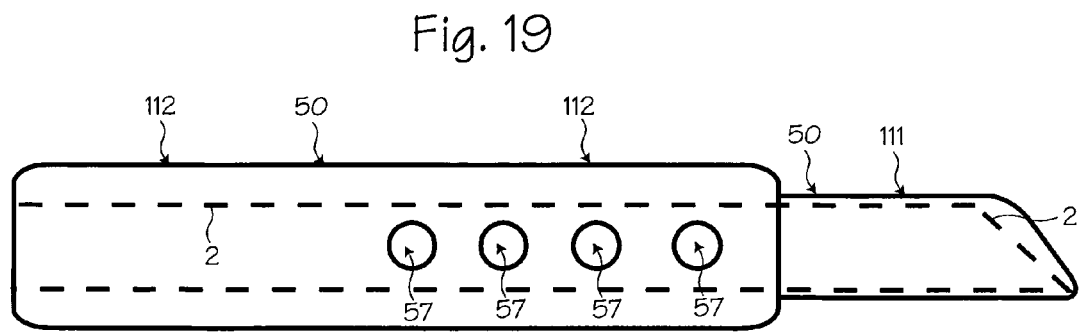

ATRAUMATIC ARTHROSCOPIC INSTRUMENT SHEATH

This application is a continuation-in-part of U.S. application Ser. No. 10/769,629 filed Jan. 29, 2004.

FIELD OF THE INVENTIONS

The inventions described below relate the field of arthroscopic surgical instruments.

BACKGROUND OF THE INVENTIONS

Medical science has long sought ways to minimize the dangers and trauma inherent in invasive surgical procedures. To this end, surgical techniques and instruments have been developed which, among other things, reduce the size and number of the incisions required to perform various surgical procedures. These techniques and instruments have been remarkably successful. Procedures that only a few years ago would require multiple incisions several inches in length, are today being performed with just a few one-ince incisions.

During minimally evasive surgeries, surgical instruments such as trocars, cannulas, and optical medical devices, including endoscopes, cystoscopes, arthroscopes, laparoscopes, etc., are inserted through small incisions or portals in a patient's body or body cavity and manipulated to perform surgical procedures within the patient.

Minimally invasive surgical procedures are safer than open surgery and result in quicker patient recovery, shorter hospital stays, and lower health care costs. Accordingly, minimizing invasiveness continues to be of importance, and there is a continuing need for devices and methods that achieve this objective.

One significant barrier to further minimizing the invasiveness of surgery is the necessity of many surgical instruments to have fluid channels. These channels effectively add to the outer diameter of the instruments. For example, known endoscopic instruments provide inflow/outflow through an assembly of concentric sheaths that define channels for inflow and outflow of fluids to and from the operative or surgical site. The fluid may be an irrigating solution that helps maintain a clear view of the site for the physician. Certain known irrigating systems provide simultaneous and continuous inflow and outflow. These systems are known as "continuous flow" systems.

The known inflow and outflow endoscope systems introduce an irrigating fluid into the surgical site. For this purpose, the endoscope has an inflow channel defined by the inner surface of the inner sheath. The fluid passes through the channel and exits the distal end of the sheath to irrigate the operative site. Fluid at the surgical site may be withdrawn through an outflow channel defined by the outer surface of the inner sheath and the inner surface of a surrounding outer sheath. The outflow channel originates at the distal end (front end) of the instrument and transports fluid to an exit point at the proximal end of the outer sheath. The diameter of these systems require larger surgical portals.

Another barrier to minimally invasive surgery is the number of incisions or portals required by the surgeon in order to perform a surgical procedure. During many procedures, multiple portals are required to provide irrigation of the surgical site and removal of debris, view the surgical site with use of an endoscope, and facilitate the use of specialized surgical equipment to repair the injury or abnormality. Each incision creates additional risk of infection and extends recovery time.

A procedure where less invasive surgical techniques may be beneficial is arthroscopic surgery. Presently, arthroscopic surgical techniques use a standard three-portal (incision) technique. A first portal is made in the patient and then used to insert an arthroscope to view the surgical site. A second portal is created to insert a specialized surgical instrument to correct the injury or abnormality. Also, a third portal is usually made and then used to insert an inflow cannula to distend the joint. The inflow cannula is used to fill the joint with a sterile fluid to expand the joint and make room for the surgeon to see and work. After the procedure, the joint is washed out with a stream of fluid, the instruments are removed, and the portals are closed with stitches, staples, or Steri-strips. Having multiple portals, coupled with larger sized portals due to the size of the medical instruments, can be a source of postoperative pain and may inhibit postoperative recovery.

In arthroscopic surgery, as well as other surgical procedures, there remains a significant need for improved techniques that reduce the number of portals used by surgeons as well as reduce the size of the portals while providing continuous fluid inflow and outflow. The Applicant's improved inflow/outflow sheath reduces the diameter of the continuous flow system while eliminating the need for a third portal during arthroscopic surgery.

SUMMARY

The devices and methods shown below provide for smaller and fewer surgical portals during arthroscopic surgery while also providing substantially simultaneous inflow and outflow of fluid to the surgical site. The distal end of the atraumatic sheath extends slightly past the distal end of the rigid cannula, thereby providing a soft, blunt cushion over the distal end of the rigid cannula. The atraumatic sheath thereby protects any surrounding tissue or objects from accidental injury or damage while the arthroscope is manipulated inside the operating field.

The atraumatic sheath may also be provided as an inflow/outflow sheath that allows a surgeon to drain fluids from or introduce fluids into the surgical field, thereby keeping the surgical field clear. The inflow/outflow sheath is a multi-lumen tube into which the arthroscope is inserted. The proximal portion of the sheath is provided with fluid ports, a manifold and other means of controlling the flow of fluid inside the sheath. The distal portion of the inflow/outflow sheath is provided with a plurality of holes. Each hole communicates with one or more of the lumens inside the tube, thereby allowing fluid to flow between the surgical field and sources or sinks located outside the patient. The inflow/outflow sheath thereby allows the surgeon to maintain a clear surgical field and protect the patient from accidental injury while eliminating the need for a third irrigation instrument.

BRIEF DESCRIPTION OF THE DRAWINGS

FIG. 5 shows a cross section of the atraumatic sheath shown in FIG. 2 and an arthroscopic instrument disposed inside the atraumatic sheath.

FIG. 6 shows an inflow/outflow atraumatic sheath for use with arthroscopic instruments.

FIG. 7 shows an inflow/outflow atraumatic sheath for use with arthroscopic instruments and an arthroscope disposed inside the atraumatic sheath.

FIG. 8 shows a cross section of the distal portion of the inflow/outflow atraumatic sheath of FIG. 7.

FIG. 9 shows a cross section of the distal portion of an inflow/outflow atraumatic sheath.

FIG. 10 shows a cross section of the distal portion of an inflow/outflow atraumatic sheath.

FIG. 11 shows a cross section of the distal portion of an inflow/outflow atraumatic sheath.

FIG. 12 shows a cross section of the distal portion of an inflow/outflow atraumatic sheath.

FIG. 13 shows a cross section of the distal portion of an inflow/outflow atraumatic sheath.

FIG. 14 shows a cross section of the distal portion of an inflow/outflow atraumatic sheath.

FIG. 15 shows a cross section of the distal portion of an inflow/outflow atraumatic sheath.

FIG. 16 shows a cross section of the distal portion of an inflow/outflow atraumatic sheath.

FIG. 17 shows an inflow/outflow atraumatic sheath for use with arthroscopic instruments.

FIG. 18 shows a cross section of the distal portion of the inflow/outflow sheath shown in FIG. 17.

FIG. 19 shows an inflow/outflow sheath having a distal portion that has an inner diameter that closely conforms to the outer diameter of the distal portion of an arthroscope.

DETAILED DESCRIPTION OF THE INVENTIONS

Figure 1:
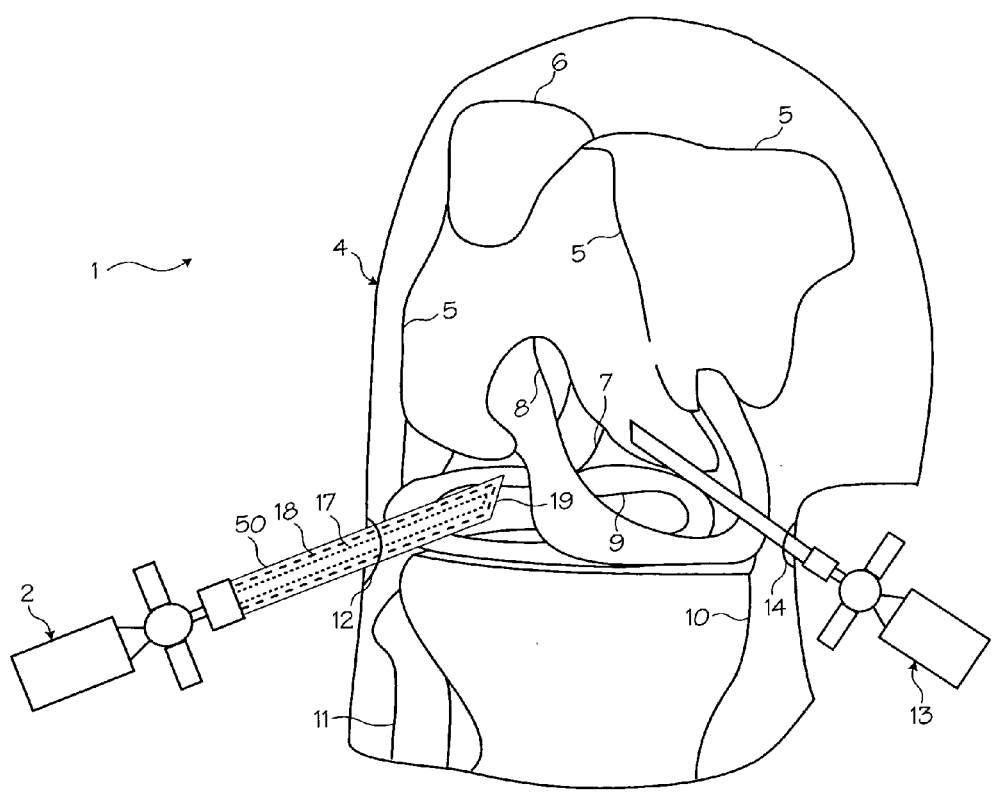
FIG. 1 shows a method of performing arthroscopic surgery on a patient.

FIG. 1 shows a method of performing arthroscopic surgery on a patient by using an arthroscopic instrument 2 sheathed in an atraumatic introducer sheath 3. An arthroscopic instrument may be an arthroscope, endoscope, awl, pick, shaver, etc. In FIG. 1, the arthroscopic instrument 2 shown is an arthroscope. (The various parts of the arthroscope are shown in phantom to indicate their positions inside the sheath.) Various anatomical landmarks in the patient's knee 4 are shown for reference, including the femur 5, patella 6, posterior cruciate ligament 7, anterior cruciate ligament 8, meniscus 9, tibia 10 and fibula 11. During surgery, the surgeon introduces the arthroscope 2 into the knee via a first incision 12 in order to visualize the surgical field. A trimming instrument 13 is introduced through a second incision 14 to remove or trim tissue that the surgeon determines should be removed or trimmed. Optionally, an irrigating instrument 15 may be introduced through a third incision 16 in order to irrigate the surgical field and thereby maintain a clear view. As provided below, the irrigating instrument may be replaced by a combined arthroscope and inflow/outflow atraumatic sheath.

The arthroscope 2 is an optical instrument 17 surrounded by a rigid cannula 18 having a distal edge that typically is cut at an angle. To protect the patient from unintended injury or trauma during the procedure, the arthroscope has been inserted into a resilient, outer introducer sheath or atraumatic sheath 3 that extends over the rigid cannula. The distal tip 19 of the atraumatic sheath extends distally just past the distal end of the arthroscope and rigid cannula to further protect the patient.

Figure 2:
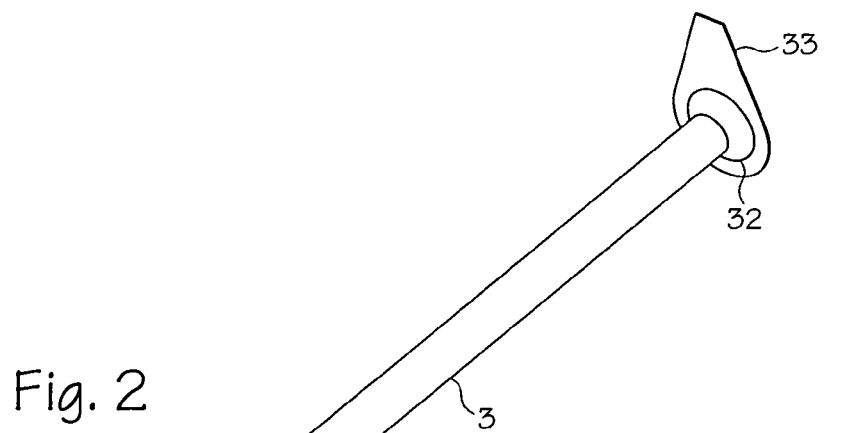
FIG. 2 shows an atraumatic sheath for use with arthroscopic instruments.
Figure 3:
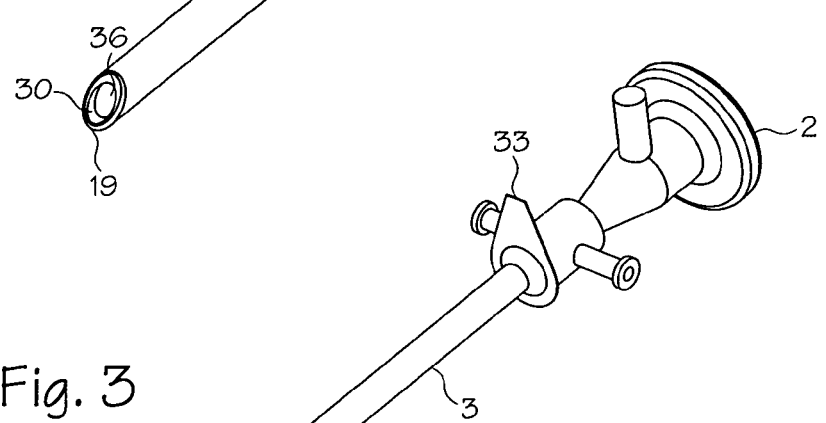
FIG. 3 shows an atraumatic sheath for use with arthroscopic instruments and an arthroscope disposed inside the atraumatic sheath.
Figure 4:
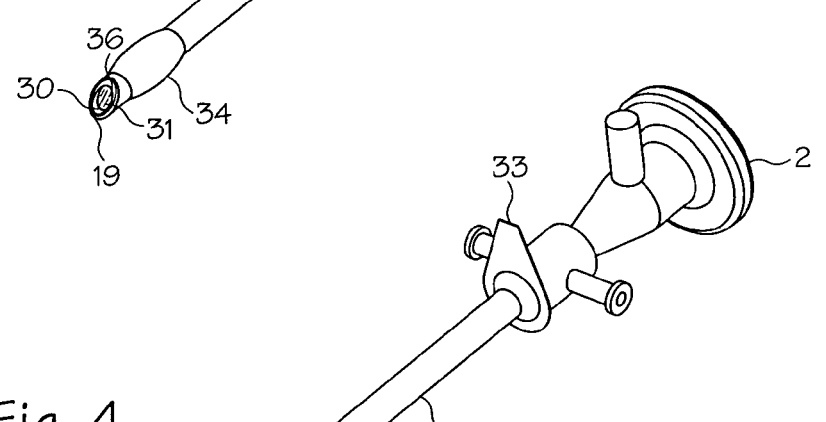
FIG. 4 shows an atraumatic sheath for use with arthroscopic instruments, an arthroscope disposed inside the atraumatic sheath and an irrigation tube disposed on the sheath.

FIGS. 2 through 4 illustrate the atraumatic sheath 3. The atraumatic sheath is a tube of a resilient material, such as a soft plastic or rubber. The inner diameter of the atraumatic sheath is sized and dimensioned to closely fit over the outer diameter of an arthroscopic instrument. The distal tip 19 of the atraumatic sheath is provided with a shape that closely approximates the shape of the distal tip of the arthroscope and/or the rigid cannula. A flange 30 disposed around the distal end of the sheath prevents the distal tip of the rigid cannula from gouging the patient. The flange is integral with the walls of the sheath and extends inwardly towards the axis of the sheath. The flange is sized and dimensioned to prevent the distal tip of the rigid cannula from accidentally slipping distally during a surgical procedure. An opening 36 is provided in some atraumatic sheaths so that the surgeon may insert the endoscope or other instruments through the opening and into the surgical space. The distal lens 31 of an optical instrument is shown for reference in FIGS. 3 and 4.

The proximal end 32 of the atraumatic sheath is provided with a tab 33 to allow medical personnel to easily pull the atraumatic sheath over the rigid cannula, arthroscope and/or arthroscopic instrument. The proximal end of the atraumatic sheath may also be provided with fittings 38, such as a locking hub or snap latches, that attach to fittings 39 or openings disposed on the arthroscope or other instrument, thereby securing the atraumatic sheath as illustrated in FIG. 7.

The outer surface of the atraumatic sheath may be provided with a smooth coating 40 as shown in FIG. 5 to allow the arthroscope and rigid cannula to more easily move within an operating site. For example, the sheath may be provided with a Teflon® (PTFE or expanded polytetrafluoroethylene) coating or covered with a water-activated lubricant. In contrast, the inner surface of the atraumatic sheath (the walls that define the lumen of the tube) may be provided with a non-slip coating 41 or other high coefficient of friction coating. For example, the inner surface of the atraumatic sheath may be coated with a co-extruded tacky thermoplastic elastomer (TPE). The non-slip coating prevents the sheath from easily slipping over the outer surface of the rigid cannula or arthroscope, thereby helping to prevent the atraumatic sheath from twisting or slipping around the arthroscope.

FIGS. 3 and 4 show an atraumatic sheath 3 for use with arthroscopic instruments and an endoscope or arthroscope 2 disposed inside the atraumatic sheath. The atraumatic sheath shown in FIG. 3 is provided with a balloon 34 on the distal portion of the sheath. (The balloon may be integrally formed with the sheath.) The balloon allows a surgeon to open a space within tissue, thereby dissecting the surgical field. The arthroscope may then be extended distally out of the opening 36 and the surgical space visualized. In addition, the distal end of the sheath may be provided with a distally projecting spoon or other distally projecting object to prop open a space in front of the arthroscope. The balloon and the distally projecting spoon thus provide a means for dissecting or retracting tissue to form a small surgical space.

FIG. 4 shows an atraumatic sheath 3 having a second, working tube 35. The working tube allows irrigation, fiber optics, sutures, needles, probes or surgical tools through the lumen. The atraumatic sheath shown in FIG. 4 may be combined with the atraumatic sheath shown in FIG. 3 to provide an atraumatic sheath with both a balloon and a working tube.

FIG. 5 shows a cross section of the atraumatic sheath 3 shown in FIG. 2 and an arthroscopic instrument 2 disposed inside the sheath. The atraumatic sheath is provided with a tab 33 on the proximal end of the sheath in order to increase the ease of pulling the sheath over the arthroscope. The distal end of the sheath is provided with an opening 36 to allow light to pass between the arthroscope and the operating space and, optionally, to allow additional instruments to pass through or alongside the arthroscope and into the surgical field. The walls 37 of the sheath at the distal end 19 of the sheath are thicker than the rest of the sheath walls to form a flange 30 at the distal end of the sheath. (The flange may be a separate ring of material attached to the inside of the sheath.) The flange covers the sharp distal tip of the arthroscopic instrument and prevents the instrument from slipping distally through opening 36. The rest of the walls of the atraumatic sheath are thin in order to minimize the overall thickness of the combined sheath and arthroscopic instrument.

In use, the atraumatic sheath is provided and pulled over an arthroscopic instrument. (The instrument may also be thought of as being inserted into the sheath.) The sheathed arthroscopic instrument is then inserted into the surgical site and the surgeon performs a medical procedure therein. If a balloon is provided, the balloon is used to dissect tissue so that the arthroscope may be extended distally out of the opening 36 and the surgical space visualized.

FIGS. 6 and 7 show an inflow/outflow atraumatic sheath 50 and an arthroscope 2 disposed inside the sheath. Like the sheath shown in FIG. 2, the inflow/outflow atraumatic sheath 50 is formed of a resilient material that protects the patient from accidental injury should the arthroscope poke at or scrape along tissue. The sheath material may also be radiopaque. A preferred durometer hardness of the sheath material is in the range of about 40 Shore A to about 90 Shore D. In this hardness range the sheath is sufficiently resilient that the sheath protects the patient from accidental injury but is sufficiently hard to prevent the lumens within sheath from collapsing.

The inflow/outflow sheath 50 is a multi-lumen tube into which an arthroscope is inserted. Each lumen extends from the distal portion 51 of the sheath to the proximal portion 52 of the sheath. The proximal portion of the sheath is provided with one or more fluid ports, such as first port 53 or second port 54; one or more stopcocks 55 or fluid switches; one or more valves, such as an anti-backflow valve; a manifold 56; or other means of controlling the flow of fluid inside the sheath. The distal portion 51 of the inflow/outflow sheath is provided with a plurality of holes 57. Each hole communicates with one or more of the lumens inside the tube, thereby allowing fluid to flow between the surgical field and the lumens inside the sheath 50. The plurality of holes 57 positioned at the distal end of the inflow/outflow sheath 50 is particularly useful during surgery. In traditional sheaths, fluid inflow and outlow occur at a single open end. The use of a single opening sheath causes debris to be suctioned directly towards the lens of the arthroscope. This results in a "snow storm" effect in a surgeons field of view during surgery. The plurality of holes located 57 on the side of the inflow/outflow sheath 50 allow debris to be suctioned away the arthroscope tip and out of the surgeon's field of view.

Prior to surgery, medical personnel or the device manufacturer inserts the arthroscope into the inflow/outflow atraumatic sheath and secures the sheath to the arthroscope via a set-screw, snap-on attachment, other releasable attachments or other means 58 for securing the sheath to the arthroscope. During use, a surgeon may cause a fluid, preferably saline, to flow from a fluid source 59, through the arthroscope and into the surgical field, as shown by inflow arrows 60. (The arthroscope is provided with one or more lumens, ports or working tubes that allow fluid to flow through the arthroscope and into the surgical field.) In turn, blood, other fluids and debris are drained from the surgical field through the holes 57, as shown by outflow arrows 61, and flow through one or more lumens in the sheath. The inflow of clear saline and the outflow of cloudy fluid and debris allow the surgeon to maintain a clear surgical field using a single instrument. In turn, this capability eliminates the need to use an irrigating instrument. Thus, the surgeon may have a clear field of view while using only a two-incision arthroscopic procedure.

FIG. 7 also shows that fluids are drained through the inflow/outflow atraumatic sheath by using a vacuum source 70 or gravity drain operatively attached to a fluid port, such as port 53, connected to the sheath manifold 56. Fluids are provided through the arthroscope 2 from a fluid source 59 (by using a pump or gravity feed) operatively attached to a fluid port, such as third port 72 or fourth port 73 connected to the arthroscope. Depending on the capabilities of the arthroscope and the surgeon's needs, the vacuum source and fluid source may be connected to different combinations of ports provided with the inflow/outflow sheath or the arthroscope. For example, the vacuum source may be attached to port 73 and the fluid source may be attached to port 72 on the inflow/outflow sheath. In this case, the surgeon may both introduce fluids into and drain fluids from the surgical site using only the inflow/outflow sheath. Thus, even if the arthroscope is incapable of introducing fluids to or draining fluids from the surgical site, the inflow/outflow sheath allows the surgeon to eliminate the need for the irrigation instrument. In any case, a pressure sensor, and flow rate control system and feedback control system may be provided to automatically monitor and control the rate of fluid flow into and out of the surgical site.

FIG. 8 shows a cross section of the distal portion of the inflow/outflow sheath 3 shown in FIG. 6. The inflow/outflow sheath 50 has a central lumen 80, bounded by inner wall 81, through which the arthroscope is inserted. The sheath has four outer lumens, including a first outer lumen 82, a second outer lumen 83, a third outer lumen 84 and a fourth outer lumen 85 bounded by the inner wall 81, the outer wall 86 and four relatively stiff ribs 87 that extend between the inner and outer walls and that run along the length of the sheath. The distal end of the sheath in the area of the outer lumens 82, 83, 84 and 85 is sealed closed and provided with a rounded shape to help prevent injury to the patient (the central lumen remains open to accommodate the arthroscopic instrument). Holes 57 or apertures disposed in the outer wall allow fluids to flow into or out of the outer lumens. For example, lumens 82 and 84 could serve as passages through which fluids are introduced into the surgical site and lumens 83 and 85 could serve as passages through which fluids are drained from the surgical site. During another surgical procedure, all four lumens could be used to either drain or introduce fluids. Thus, the surgeon has the option of using the inflow/outflow atraumatic sheath in many different modes. (In addition, the sheath may be formed with more than or fewer than the four ribs shown, so long as at least one outer lumen remains open to fluid flow after the sheath and scope have been inserted into the surgical site.)

FIGS. 9 through 16 show cross sections of the distal portion of various inflow/outflow atraumatic sheaths. FIG. 9 shows an inflow/outflow sheath having a second set of inner lumens, including a first inner lumen 100, a second inner lumen 101, a third inner lumen 102 and a fourth inner lumen 103. With this design, the surgeon can increase the rate of fluid exchange by using all of the inner lumens to introduce fluids into the surgical site and by using all of the outer lumens 82, 83, 84 and 85 to drain fluid from the surgical site (or visa versa).

FIG. 10 shows an inflow/outflow sheath 50 without an inner wall 81. Instead, the outer surface 88 of the arthroscope 2 serves as the inner wall of the sheath 50 once the arthroscope has been inserted into the sheath 2. The four, relatively stiff ribs 87 form a seal with the outer surface 88 of the arthroscope, thereby creating the four outer lumens 82, 83, 84 and 85. The ends of the ribs may be provided with elastic flanges 104 to enhance the seal made between the ribs 87 and the arthroscope 2. This configuration reduces the overall size of the combined inflow/outflow sheath and arthroscope. (If the outer wall 86 is made of an elastomeric material, then the tube can stretch radially to accommodate a variety of sizes of arthroscopes.)

As depicted in FIG. 10, the arthroscope 2 is inserted into the sheath 50 through the central lumen 80. The arthroscope 2 may or may not be covered by a secondary protective sheath prior to insertion. Once inserted, the outer surface 88 of the arthroscope 2 comes in contact with the flanges or extensions of the ribs 87. The land of a rib may also be used to contact the outer surface of the arthroscope 2 when the ribs 87 do not have flanges or extensions. The force of the outer surface 88 of the arthroscope 2 pushing against the ribs 87 and the rib flanges or rib extensions forms a seal between the ribs 87 and the outer surface 88 of the arthroscope 2. Outer lumens 82, 83, 84 and 85 are created by the ribs, the outer surface of the endoscope 88, and inner surface 89 of the outer wall 86 of the inflow/outflow sheath. The ribs act as longitudinal struts that prevent the sheath from collapsing as they support the sheath under compression. The ribs reduce the unsupported span of the thin outer wall in the traverse axis, further preventing the collapse of the sheath. The seals formed by the contact between the ribs 87 and the outer surface 88 of the arthroscope prevent fluids from flowing between the outer lumens 82, 83, 84 and 85. The outer lumens 82, 83, 84 and 85 facilitate the continuous inflow and outflow of fluids to and from a surgical site from outside the patient 1. Check valves or gates may also be coupled to the inner wall of the inflow/outflow sheath 50 within the outer lumens 82, 83, 84 and 85 to prevent outflow fluids from flowing back towards the surgical site and to prevent inflow fluids from flowing out the proximal end of the sheath.

The inflow/outflow sheath 50 depicted in FIG. 10 typically has an outer diameter measuring about 5 to 7 millimeters when the sheath is manufactured for use with arthroscopic instruments in larger joints, though this size may vary depending on the diameter of the arthroscopic instrument. When the inflow/outflow sheath is manufactured for use with arthroscopic instruments in smaller joints, the sheath 50 has an outer diameter measuring about 2 to 3 millimeters. The outer wall thickness 86 of the inflow/outflow sheath 50 is typically 1 millimeter or less depending on the extrusion and material comprising the tube. The inflow/outflow sheath 50 can fit a range of arthroscopes +/−10% of the sheath's nominal diameter. The ribs 87 extend from the inner surface of the inflow/outflow sheath inwardly and make a tight fit when the arthroscope is inserted.

A smaller outer diameter inflow/outflow sheath 50 is particularly useful in arthroscopic surgery. Due to the unique, the inflow/outflow sheath 50 has been able to achieve a 30% reduction in diameter when compared to multi-lume cannula devices requiring an inner wall of a cannula contacting the outer wall of the arthroscope. Presently, arthroscopic surgical techniques use a standard three-incision technique. A first incision is made and used to insert an inflow cannula to distend the joint. The inflow cannula is used to fill the joint with a sterile fluid to expand the joint and make room for the surgeon to see and work. A second incision is made in the patient and used to insert an arthroscope to view the surgical site. A third incision is created by the surgeon to insert a specialized surgical instrument to correct the injury or abnormality. After the procedure, the joint is washed out with a stream of fluid, the instruments are removed, and the portals are closed with stitches, staples, or Steri-strips. Recently, surgeons have begun to shift to a two-incision technique during arthroscopic. Surgeons use one incision for inserting the arthroscope and a second incision for inserting the specialized surgical instrument. This technique eliminates a third portal by using an arthroscope with an inflow and outflow sheath. Sheaths currently used for inflow and outflow, however, do not facilitate the continuous and simultaneous inflow and outflow of fluids to and from a surgical site with a sheath having a reduced diameter. Present sheaths only facilitate alternating inflow and outflow of fluids to the surgical site and these sheaths are of a larger diameter requiring the incision to be larger. When in use, the Applicant's inflow/outflow sheath 50 can facilitate the substanially simultaneous flow of fluids to and from a surgical site through the outer lumens 82, 83, 84 and 85 while requiring a smaller size incision. Substanially simultaneous inflow and outflow allows the surgeon to keep the surgical site clean and the field of view clear.

A unique feature of the Applicant's inflow/outflow sheath 50 is the allowance of outflow to exceed inflow in the sheath 50. Higher outflow capacity facilitates the removal of debris and bodily fluids from the surgical site. Fluid pressure supplied to the inflow/outlow sheath 50 is usually standard arthroscopic distension pressure at a pressure head of approximately 6 feet to 8 feet of water, but this may vary depending on the surgical application. Suction for use with the inflow/outflow sheath 50 ranges from approximately 0 to 250 mm/Hg depending on the sheath size and surgical application. When the inflow/outflow sheath is used in conjunction with a 5.7 mm arthroscope, the inflow of fluid to a surgical site can be performed at the rate of 800 ml/min at 6 feet of water while outflow from the surgical site can be accomplished at the rate of 850 ml/min at 21 mm/Hg suction. The higher outflow capacity is able to remove both the irrigation fluid and the additional debris and bodily fluid coming from the patient during surgery.

FIG. 11 shows an inflow/outflow atraumatic sheath 50 similar to that shown in FIG. 10. The relatively hard ribs 87 are pleated, but still form a seal with the outer wall of the arthroscope 2, thereby forming the lumens 82, 83, 84 and 85 once the arthroscope is inserted into the sheath. The sheath of FIG. 11 accommodates a variety of sizes of arthroscopes because the pleated ribs will bend to a degree necessary to accommodate larger sizes of arthroscopes, as shown in FIG. 12.

FIG. 13 shows an inflow/outflow atraumatic sheath 50 similar to that shown in FIG. 11. The ribs 87 of this sheath are elastic tubes that form a seal with the outer wall of the arthroscope 2, thereby forming the outer lumens 82, 83, 84 and 85 once the arthroscope is inserted into the sheath. The sheath of FIG. 13 accommodates a variety of sizes of arthroscopes since the tubes will compress to a degree necessary to accommodate larger sizes of arthroscopes, as shown in FIG. 14.

FIG. 15 shows a "C"-shaped or slit inflow/outflow sheath 50. Like the sheath of FIG. 8, four outer lumens 82, 83, 84 and 85 are provided, with the outer lumens bounded by three ribs 87, the inner wall 81 and the outer wall 86. When the arthroscope 2 is inserted into the sheath, a small gap 105 may form between the respective tips of the first arcuate segment 106 and the second arcuate segment 107. (As the arthroscope is inserted into the surgical space, tissue 108 will seal the gap and prevent fluids from leaking from the surgical space to outside the body.) The sheath of FIG. 15 accommodates a variety of sizes of arthroscopes since the arcuate segments will move radially outwardly as a larger arthroscope is inserted into the sheath, as shown in FIG. 16.

Optionally, a protrusion or a guide rail 109 may extend from either the arthroscope or the sheath. The guide rail helps the user align the sheath on the arthroscope while inserting the arthroscope into the sheath. The guide rail also prevents unwanted rotation or twisting of the sheath over the arthroscope during a surgical procedure.

FIGS. 17 and 18 show an inflow/outflow atraumatic sheath 50 and an arthroscope 2 inserted into the sheath. In contrast to the inflow/outflow sheaths shown in FIGS. 6 through 16, the outer wall 86 of the distal portion 51 of the sheath is made from a continuous tube (the distal portion of the sheath is not provided with holes). Nevertheless, like the sheath of FIG. 8 the sheath of FIG. 17 has an inner lumen to accommodate the arthroscope and four outer lumens to accommodate fluid inflow and outflow, including a first outer lumen 82, a second outer lumen 83, a third outer lumen 84, and a fourth outer lumen 85. The outer lumens are bounded by the inner wall 81, outer wall 86 and supporting ribs 87. The instrument shown in FIG. 17 provides fluid inflow and outflow out of the distal end 110 of the sheath.

FIG. 19 shows an inflow/outflow atraumatic sheath 50 having a closely-conforming distal portion 111 that has an inner diameter that closely conforms to the outer diameter of the distal portion of an arthroscope 2. The fluid-conducting portion 112 of the sheath is set proximally from the closely conforming distal portion 111 of the sheath. The outer diameter of the fluid conducting portion 112 and the outer diameter of the closely conforming distal portion 111 may be formed integrally with each other such that both portions are part of the same sheath. Holes 57 disposed in the fluid-conducting portion 112 just proximally of the distal portion 111 of the sheath communicate with one or more lumens inside the sheath, thereby allowing a surgeon to either introduce or drain fluids from a surgical site. The sheath shown in FIG. 19 has a distal portion 111 with a relatively small radius, since the sheath closely conforms to the arthroscope at the distal portion of the arthroscope. This provides the surgeon with the capability of inserting the arthroscope into narrow surgical sites. In addition, the fluid-conduction portion still allows a surgeon to irrigate the surgical field with the combined sheath/arthroscope instrument.

Figure 20:
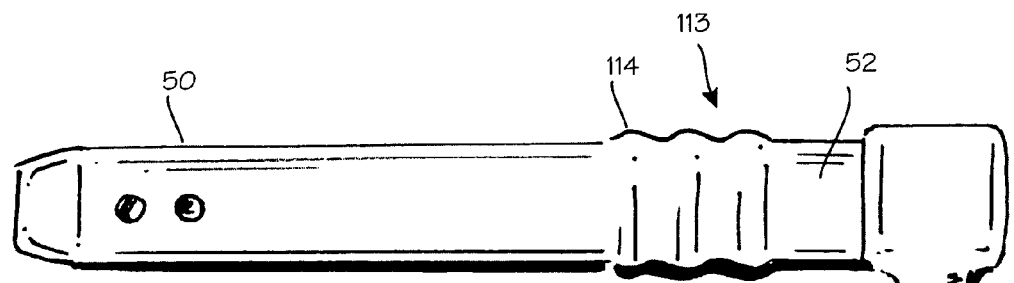
FIG. 20 shows a continuous inflow/outflow atraumatic sheath with a tissue retention feature in the shape of radially extending ridges.
Figure 21:
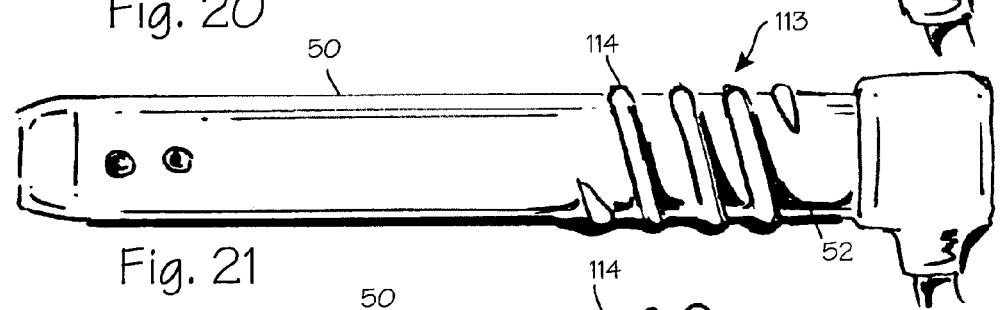
FIG. 21 shows a continuous inflow/outflow atraumatic sheath with a tissue retention feature in the shape of a threaded screw.

FIGS. 20 and 21 shows a continuous inflow/outflow atramatic sheath 50 with a tissue retention feature 113. The outer surface of the proximal portion 52 of the sheath is corrugated or provided with ridges 114 that engage the tissue surrounding the surgical site and help prevent the sheath or instrument from being unintentionally forced out of the operating field. The ridges 114 of the tissue retention feature 113 are circumferentially disposed around the sheath and may be in the shape of straight ridges extending radially outward as illustrated in FIG. 20. The ridges 114 of the tissue retention feature 113 may also be in the shape of a threaded screw as illustrated in FIG. 21.

Figure 22:
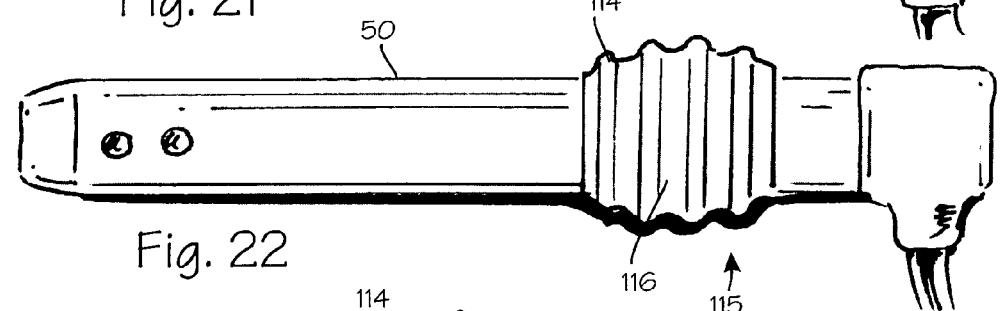
FIG. 22 shows a tissue retention module disposed over an atraumatic sheath.
Figure 23:
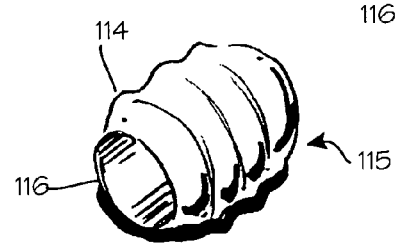
FIG. 23 shows a tissue retention module.

FIGS. 22 and 23 illustrate how the tissue retention feature is incorporated into a separate tissue retention sleeve 115 for use over an atraumatic sheath 50 not having tissue retention feature 113. In this embodiment, the tissue retention sleeve has an inner diameter so sized and dimensioned to fit over an atraumatic sheath. The tissue retention sleeve is manufactured from an elastomer having a coefficient of friction that prevents the module from moving easily once the module has been forcibly slid into position over the outer surface of the atraumatic sheath. The sleeve friction fits over the surgical instrument or atraumatic sheath. The outer surface of the tissue retention sleeve is corrugated or is provided with ridges to help prevent the sheath or instrument from being unintentionally forced out of the operating field when the sheath or instrument is provided with the tissue retention sleeve. The ridges 114 on the sleeve are circumferentially around the outer surface of the module 114 and may be in the shape of straight ridges extending radially outward. The ridges 114 may also be in the shape of a threaded screw.

The atraumatic sheath configurations may be designed or sized and dimensioned to conform to differently shaped instruments, the sheath is also useful with other medical instruments and other surgical procedures in which it is desirable to protect surrounding tissue from accidental trauma. For example, the atraumatic sheath may be disposed over a trimming instrument for use during arthroscopic surgery or over an energy-delivering medical instrument, such as a laser or RF energy instrument. Other procedures in which the atraumatic sheath is useful include laparoscopic surgery and other kinds of endoscopic surgery. In addition, the various sheath configurations shown herein may be combined to form additional types of instrument sheaths. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for performing arthroscopic surgery, said system comprising:
   an arthroscopic instrument suitable for performing an arthroscopic surgical procedure; and
   an atraumatic sheath having an inner diameter sized and dimensioned to permit fluid flow between an inner surface of the sheath and an outer surface of the arthroscopic instrument disposed within the sheath, said sheath further having a plurality of ribs extending inwardly from the inner surface of said sheath and running longitudinally along said sheath;
   wherein said ribs define outer lumens between the outer surface of the arthroscopic instrument and the inner surface of the sheath;
   wherein the atraumatic sheath is adapted to be removably disposed over the arthroscopic instrument;
   wherein said ribs further comprise flanges.

2. The system of claim 1 wherein the sheath is characterized by an outer surface, wherein said outer surface is provided with a smooth coating.

3. The system of claim 1 further comprising a fluid source in fluid communication with one or more outer lumens in the sheath.

4. The system of claim 1 further comprising a vacuum source.

5. The system of claims 1, 3, or 4 further comprising a control system controlling the inflow and outflow of fluid to the surgical site.

6. The system of claim 5 wherein the outflow of fluid equals or exceeds the inflow.

7. The system of claim 3 further comprising a vacuum source.

8. The system of claim 7 further comprising a control system controlling the inflow and outflow of fluid to the surgical site.

9. The system of claim 1 further comprising check valves coupled to the inner surface of said sheath within the outer lumens.

10. The system of claim 1 further comprising a first set of fittings disposed on the proximal end of the sheath and a second set of fittings disposed on the arthroscopic instrument, wherein the first and second sets of fittings are adapted for releasable coupling, whereby the sheath is secured to the arthroscopic instrument when the first and second sets of fittings are secured together.

11. The system of claim 1 wherein the atraumatic sheath is characterized by a distal portion, said distal portion having a plurality of holes in fluid communication with one or more lumens and the surgical site.

12. An atraumatic sheath comprising:
a tube characterized by a distal portion, a proximal portion, an outer surface, an inner surface, an inner diameter and an outer diameter;
wherein the inner diameter of said tube is sized and dimensioned to permit fluid flow between the inner surface of the tube and an outer surface of an arthroscopic instrument when the arthroscopic instrument is disposed within the tube; and
a plurality of ribs extending inwardly from the inner surface of the tube and running longitudinally along the tube;
wherein said ribs further define outer lumens between the outer surface of the arthroscopic instrument and the inner surface of the tube;
wherein said ribs further comprise flanges, said flanges forming a seal between the ribs and the outer surface of an arthroscopic instrument when the arthroscopic instrument is disposed within the sheath.

13. The atraumatic sheath of claim 12 further comprising check valves coupled to the inner surface of the tube within the outer lumens, said anti-backflow gates operable to prevent the back flow of fluid within the lumens.

14. The atraumatic sheath of claim 12 wherein said distal portion further comprises a plurality of holes in fluid communication with one or more outer lumens and a surgical site.

15. A method of performing arthroscopic surgery, said method comprising the steps of:
providing a system for performing arthroscopic surgery, said system comprising:
an arthroscopic instrument suitable for performing an arthroscopic surgical procedure;
an atraumatic sheath having an inner diameter sized and dimensioned to permit fluid flow between an inner surface of the sheath and an outer surface of the arthroscopic instrument disposed within the sheath, said sheath further having a plurality of ribs extending inwardly from the inner surface of said sheath and running longitudinally along said sheath;
wherein said ribs define outer lumens between the outer surface of the arthroscopic instrument and the inner surface of the sheath, said outer lumens facilitating the inflow and outflow of fluid to and from a surgical site;
wherein said ribs further comprise flanges;
wherein the atraumatic sheath is adapted to be removably disposed over the arthroscopic instrument;
placing the arthroscopic instrument inside the sheath; and
performing an arthroscopic surgical procedure with the system for performing arthroscopic surgery.

16. The method of claim 15 further comprising the step of providing substantially simultaneous inflow and outflow of fluid to an arthroscopic surgical site.

17. The method of claim 15 further comprising the step of providing substantially simultaneous inflow and outflow of fluid to an arthroscopic surgical site wherein the outflow of fluid is at a rate equal to or exceeding the inflow rate of fluid.

18. The method of claim 15 wherein the atraumatic sheath is characterized by a distal portion, said distal portion having a plurality of holes in fluid communication with one or more lumens and the surgical site.

* * * * *